(12) United States Patent
Utas et al.

(10) Patent No.: US 9,408,946 B2
(45) Date of Patent: Aug. 9, 2016

(54) URINARY CATHETER

(75) Inventors: Jan Utas, Kungsbacka (SE); Fredrik Andersson, Mölndal (SE)

(73) Assignee: Astra Tech AB, Mölndal (SE)

( * ) Notice: Subject to any disclaimer, the term of this patent is extended or adjusted under 35 U.S.C. 154(b) by 0 days.

(21) Appl. No.: 13/438,457

(22) Filed: Apr. 3, 2012

(65) Prior Publication Data

US 2012/0191073 A1 Jul. 26, 2012

Related U.S. Application Data

(62) Division of application No. 11/488,099, filed on Jul. 18, 2006, now Pat. No. 8,168,249.

(30) Foreign Application Priority Data

Jul. 18, 2005 (SE) ........................ 0501696

(51) Int. Cl.
*A61M 39/00* (2006.01)
*A61L 29/00* (2006.01)
*A61L 29/04* (2006.01)
*A61L 29/14* (2006.01)

(52) U.S. Cl.
CPC ............... *A61L 29/049* (2013.01); *A61L 29/14* (2013.01)

(58) Field of Classification Search
CPC ....... A61M 1/00; A61M 21/00; A61M 25/00; A61M 31/00; A61M 39/00
USPC .............................. 604/540–544; 427/2.1, 2.3
See application file for complete search history.

(56) References Cited

U.S. PATENT DOCUMENTS

| | | | |
|---|---|---|---|
| 4,373,009 A | 2/1983 | Winn | |
| 4,487,808 A | 12/1984 | Lambert | |
| 4,616,064 A | 10/1986 | Zukosky et al. | |
| 4,906,237 A | 3/1990 | Johansson et al. | |
| 5,356,709 A | 10/1994 | Woo et al. | |

(Continued)

FOREIGN PATENT DOCUMENTS

| | | |
|---|---|---|
| EP | 0 496 305 A2 | 1/1992 |
| EP | 0 669 142 A2 | 8/1995 |

(Continued)

OTHER PUBLICATIONS

Chart, Shore a Hardness vs. Shore D hardness, http://www.calce.umd.edu/TSFA/Hardness_ad_.htm, Fig. 5, p. 10.

*Primary Examiner* — Melanie Hand
(74) *Attorney, Agent, or Firm* — Birch, Stewart, Kolasch & Birch, LLP

(57) ABSTRACT

A medical device is disclosed, comprising a substrate, having on its surface, on at least a part thereof, a hydrophilic surface layer providing low-friction surface character of the medical device when wetted by a wetting fluid. The substrate is made of a polymer blend comprising a polyolefin and a composition having molecules with active hydrogen(s), such as polyamide or polyurethane. The hydrophilic surface layer is preferably adhered to the substrate by a polyurea network, whereby said polyurea network forms a covalent bond to said active hydrogen(s) in the substrate. The new substrate material is environmentally acceptable and cost effective, has adequate mechanical and chemical properties and enables the hydrophilic coating to be adequately adhered.

21 Claims, 1 Drawing Sheet

(56) References Cited

U.S. PATENT DOCUMENTS

| | | |
|---|---|---|
| 5,554,120 A | 9/1996 | Chen et al. |
| 5,871,823 A | 2/1999 | Anders et al. |
| 6,080,488 A | 6/2000 | Hostettler et al. |
| 7,018,372 B2 | 3/2006 | Casey et al. |
| 7,297,159 B2 | 11/2007 | Hossainy et al. |
| 7,335,185 B2 | 2/2008 | Tang et al. |
| 7,387,810 B2 | 6/2008 | Hossainy |
| 2001/0011165 A1 | 8/2001 | Engelson et al. |
| 2002/0002363 A1 | 1/2002 | Urakawa et al. |
| 2002/0018898 A1 | 2/2002 | Opolski |
| 2002/0077606 A1 | 6/2002 | Trotta |
| 2003/0232931 A1 | 12/2003 | Chen et al. |
| 2004/0153051 A1 | 8/2004 | Israelsson et al. |
| 2004/0175558 A1 | 9/2004 | El-Nounou et al. |
| 2008/0061002 A1 | 3/2008 | Sugaya et al. |

FOREIGN PATENT DOCUMENTS

| | | |
|---|---|---|
| EP | 0 963 796 A2 | 12/1999 |
| EP | 1 149 598 A2 | 4/2001 |
| EP | 1149598 A2 | 10/2001 |
| JP | 8-127677 A | 5/1996 |
| JP | 2002-11092 A | 1/2002 |
| JP | 2002-541310 A | 12/2002 |
| WO | WO 97/49437 A1 | 12/1997 |
| WO | WO 00/61205 A1 | 10/2000 |
| WO | WO 03/031533 A1 | 4/2003 |
| WO | WO 2007/011287 A1 | 1/2007 |

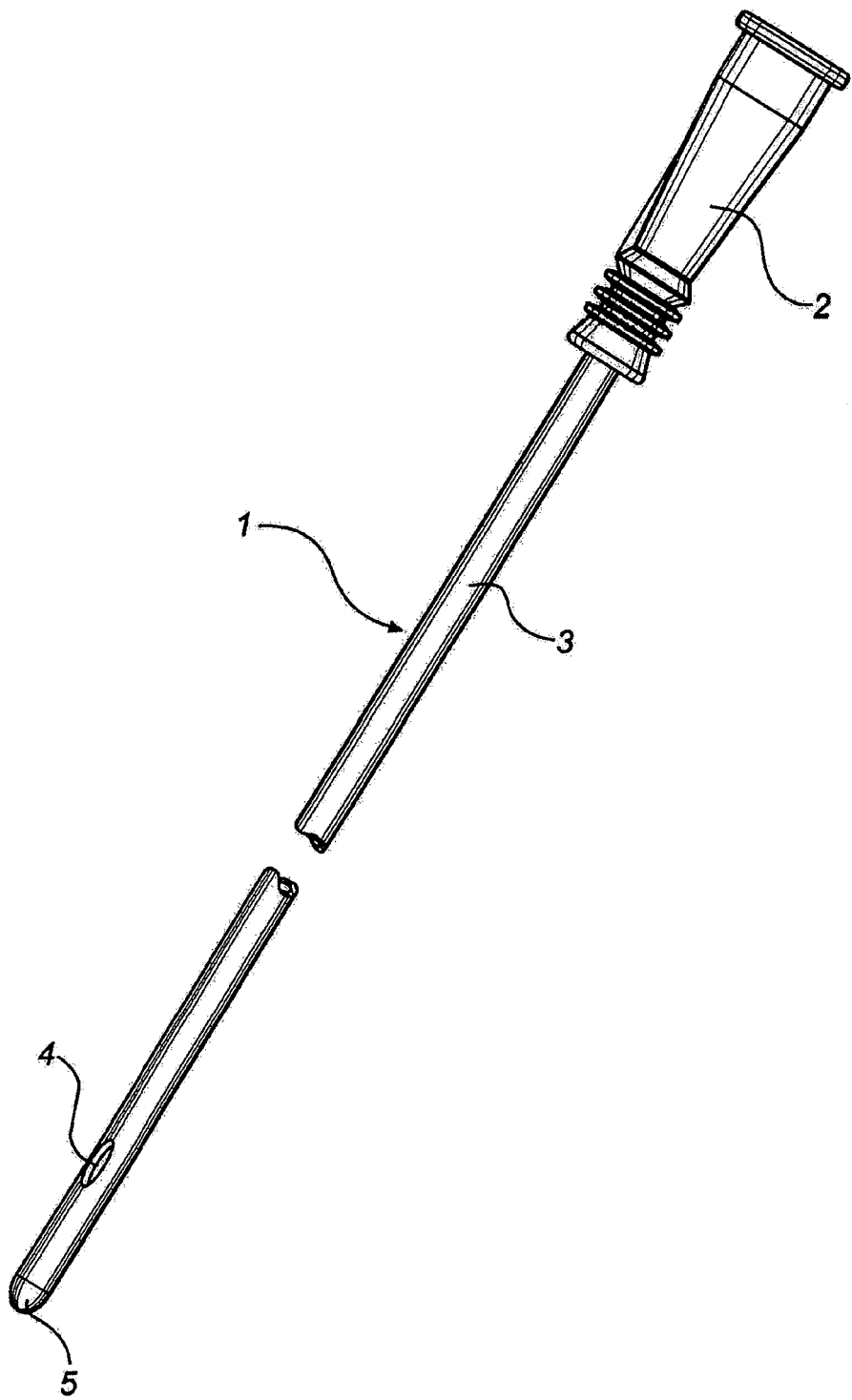

URINARY CATHETER

CROSS-REFERENCE TO RELATED APPLICATIONS

This application is a Divisional of U.S. patent application Ser. No. 11/488,099 filed on Jul. 18, 2006 now U.S. Pat. No. 8,168,249, which claims priority to Sweden Application No. 0501696-9, filed on Jul. 18, 2005. The entire contents of which are hereby incorporated by reference.

FIELD OF THE INVENTION

The present invention generally relates to medical devices which present a substrate, such as an elongate shaft, having an outer hydrophilic surface coating. In particular the invention relates to a catheter for insertion into a passageway in a human or animal body, and specifically urinary catheters. The invention is also related to a corresponding method of manufacture and use.

BACKGROUND OF THE INVENTION

Many medical devices incorporate elongate shafts such as tubes which are intended for insertion into and through passageways of a living body such as those of the urethral tract and the cardiovascular system. The most common type of this general grouping of medical devices is known as catheters. Exemplary catheters include those designated for urological, angioplasty and valvuloplasty uses, that is, adapted respectively for insertion into the urethra, the lumen of a blood vessel and heart passageway of a living body, normally a human body.

Because of the intended use of such medical devices certain parameters need to be satisfied by the material from which the elongate shaft is manufactured. The material must fulfill such requirements as softness, good kink resistance, good dimensional stability, processability, for example ease to form and glue, and the possibility to be sterilized by radiation, steam, ethylene oxide or other means. For some products, there is further the need for the material to accept a surface treatment which will impart desired surface properties to the medical device, such as hydrophilicity. To this latter end, the chemistry of the substrate material is critical since this affects the possibility to coat the substrate.

For many years now polyvinyl chloride (PVC) has been used to manufacture medical devices having elongate shafts for insertion into a body passageway such as catheters due to PVC fulfilling the requirements mentioned in the preceding paragraph. For instance, EP 0 093 093 by the same applicant makes known a process for manufacturing a PVC urinary catheter having a hydrophilic outer surface coating which exhibits a low coefficient of friction when wetted.

However, the suitability of PVC for medical devices such as catheters is now being questioned on environmental grounds and further because of the toxicity of the plasticizers added to PVC. Moreover, coating PVC catheters by, for example, the EP 0 093 093 results in an appreciable shrinkage of the PVC catheters in the longitudinal direction, typically 6-7% of the original length, due to the operating temperatures used in the coating process. The obvious disadvantage of such appreciable shrinkage is the wastage of material in the sense that PVC catheters of longer length than finally required have to be used to account for the shrinkage. In addition, quality control of the coating process is made more complicated than would be ideal by this marked degree of shrinkage.

Other substrate materials have also been proposed. For example, WO 97/49437 by the same applicant proposes to use a polyether block amide and a styrene block copolymer as substrate material for a hydrophilic catheter. These materials have proven to be suitable for hydrophilic coating, and to have adequate mechanical and chemical properties. However, a problem with these materials is that these materials are relatively expensive to manufacture. Further, polyether block amide has relatively high resilience, which makes it unsuitable for certain applications. For example, catheters made of this material may be difficult to handle for disabled patients. When using styrene block copolymer, the adherence of surface coatings, such as hydrophilic coatings, is lower than when using e.g. polyether block amide.

Thus, there is a general problem for most previously known catheter substrates, that they are costly and/or harmful to the environment, and/or that there are problems related to the hydrophilic coating, such as too poor water retention properties, especially after leaching, too poor adherence to the substrate and too high friction of the hydrophilic surface when wetted. Further, alternatively or additionally, the mechanical properties of the substrates may be inadequate, such as being too stiff or having too high resilience.

There is therefore a need for a new substrate material for medical devices to be coated with a hydrophilic surface coating, which is environmentally acceptable and cost effective, to which the hydrophilic coating can be adequately adhered, and which has adequate mechanical and chemical properties.

SUMMARY OF THE INVENTION

It is a general object of the present invention to alleviate the above-discussed problems.

According to a first aspect of the invention, there is provided a medical device comprising a substrate, having on its surface, on at least an insertable part thereof, a hydrophilic surface layer providing low-friction surface character of the medical device when wetted by a wetting fluid, wherein the substrate is made of a polymer blend comprising a polyolefin and a composition having molecules with active hydrogen(s). Preferably, the substrate consists of such a polymer blend of polyolefin and a composition having molecules with active hydrogen(s).

Molecules with active hydrogen(s) are molecules having hydrogen that is prone to react with other substances, and thus to leave its position in the molecule. Examples of such compositions having molecules with active hydrogen groups are alcohols, amides, amines, urethanes and acids.

This substrate is based on polyolefin. Polyolefin is a material comprising olefin monomers, such as one or several of ethylene, propylene, styrene, butadiene, pentene, etc. The polyolefin can comprise intermixed medical oil and/or paraffin. Polyolefins can be made cost effective and with good mechanical properties for use e.g. as a catheter, and in particular for urinary catheters, and with good environmental properties. However, with polyolefin substrates it is relatively difficult to obtain a good adherence for a hydrophilic surface coating. However, it has now surprisingly been found by the present inventors, that a polymer blend comprising a polyolefin and a composition having molecules with active hydrogen(s) maintains the excellent mechanical properties of the polyolefin, but in addition provides excellent adherence properties for a hydrophilic surface coating. Consequently, this new substrate material surprisingly combines excellent adherence properties for a hydrophilic surface coating and excellent mechanical and chemical properties, and at the same time the material is environmentally acceptable and cost effective.

In experiments it has been concluded that when this novel substrate composition is coated with a hydrophilic coating, it provides excellent water retention, both before and leaching, and excellent low-friction properties of the surface when wetted with a wetting fluid, both immediately after wetting and for an extended period of time.

Different blend compositions may be used. However, it is preferred that the polymer blend comprises at least 80 weight percent of polyolefin and therein possibly intermixed medical oil and/or paraffin. Further, it is preferred that the polymer blend-comprises a weight percentage of the composition having molecules with active hydrogen(s) in the range of 2-20, and preferably in the range 3-15 and most preferably in the range 5-10.

Preferably, the composition having molecules with active hydrogen(s) is a polymer having active hydrogen(s), and most preferably a polymer having active hydrogen(s) bound to the polymer via nitrogen. In particular, polyamide and polyurethane has proven very effective to this end. However, it is also possible to use other polymers having active hydrogen(s), and also non-polymer compositions and substances are feasible. For example, glycerol, glycol, butanediol, di-amines and tri-amines may be considered to this end.

Preferably, the polymer blend of the substrate is essentially free from chlorine or other halogens.

In order to obtain good mechanical properties, the substrate preferably has a hardness Shore A in the range 75-85, and preferably within the range 78-82. It is further preferred that the substrate has a melting temperature exceeding 90 deg. C., and preferably exceeding 110 deg. C., and most preferably exceeding 130 deg. C.

It is further preferred to make the substrate have a radiation resistance such that it can endure at least 50 kGy essentially without degradation. Hereby, radiation sterilization of the medical device can be used, without affecting the properties of the medical device.

Many different types of hydrophilic coatings may be used for coating of the above-defined substrate. In a preferred embodiment, the hydrophilic surface layer is adhered to the substrate by a polyurea network, whereby said polyurea network can form a covalent bond to said active hydrogen(s) in the substrate. In a similar way, the hydrophilic surface layer may be adhered to the substrate by a polyester or epoxy network.

According to a second aspect of the invention, there is provided a method for producing a urinary catheter, comprising the steps of:

preparing a polymer blend comprising a polyolefin and a composition having molecules with active hydrogen(s);

forming a catheter substrate from said polymer blend; and coating at least an insertable part of the substrate with a hydrophilic surface layer providing low-friction surface character of the medical device when wetted by a wetting fluid.

The forming of the catheter substrate from said polymer blend is preferably made by means of extrusion or molding, such as injection molding.

Hereby, similar advantages and properties are obtained as discussed above in relation to the first aspect of the invention.

According to a third aspect of the invention, there is provided a use in a catheter substrate, to be coated with a hydrophilic surface coating, of a composition of a polymer blend comprising a polyolefin and a composition having molecules with active hydrogen(s).

Hereby, similar advantages and properties are obtained as discussed above in relation to the first and second aspects of the invention.

These and other aspects of the inventive concept will be apparent from and elicited with reference to the embodiments described hereinafter.

BRIEF DESCRIPTION OF THE DRAWINGS

By way of example embodiments of the invention will now be described with reference to the accompanying drawings in which:

FIG. 1 illustrates an embodiment of a catheter according to the invention.

DESCRIPTION OF PREFERRED EMBODIMENTS

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length of the catheter.

Hydrophilic catheters may be used for many different purposes, and for insertion into various types of body-cavities. However, the following discussion is in particular concerned with the preferred field of use, urinary catheters, even though the invention is not limited to this particular type of catheters.

A catheter 1 as illustrated in FIG. 1 comprises a flared rearward portion 2 and an elongate shaft or tube 3 projecting forwardly from the rearward portion 2. An open-ended internal lumen (not shown) extends from the rear end of the rearward portion 2 to a drainage aperture 4 in a rounded tip 5 of the elongate tube 3. The rearward portion 2 may function as a connector of the catheter 1, being connectable to other devices, such as a urine collection bag, a drainage tube or the like.

At least a part of the elongate tube 3 forms an insertable length to be inserted through a body opening of the user, such as the urethra in case of a urinary catheter. By insertable length is normally meant that length of the elongate tube 2 which is coated with a hydrophilic material, for example PVP, and which is insertable into the urethra of the patient. Typically, this will be 80-140 mm for a female patient and 200-350 mm for a male patient.

According to the invention, and applicable for the embodiments disclosed herein, many different types of well-known hydrophilic surfaces can be used. For example, the catheter may be provided with a hydrophilic coating wherein the hydrophilic polymer coating comprises material selected from polyvinyl compounds, polysaccharides, polyurethanes, polyacrylates or copolymers of vinyl compounds and acrylates or anhydrides, especially polyethyleneoxide, polyvinylpyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The preferred hydrophilic polymer is polyvinylpyrrolidone. A detailed description of a preferred coating method is provided below.

Upon use, the catheter is wetted by a wetting fluid, whereby the hydrophilic surface becomes slippery and easy to insert into e.g. the urethra of the patient, i.e. to provide a low-friction character of the surface. The wetting fluid is preferably a water-based liquid, i.e. using water as a solvent.

DESCRIPTION OF PREFERRED SUBSTRATE MATERIALS

The elongate shaft/tube of the catheter is made of a substrate material. This substrate is made of a polymer blend comprising a polyolefin and a composition having molecules with active hydrogen(s).

The polyolefin can comprise at least one polymer selected from the group: polyethylene, polypropylene, and styrene block copolymer (SEBS). The composition having molecules with active hydrogen(s) can be a polymer having active hydrogen(s) bound to the polymer via nitrogen, such as polyamide or polyurethane.

Different blend compositions may be used. However, it is preferred that the polymer blend comprises at least 80 weight percent polyolefin and therein possibly intermixed medical oil and/or paraffin, and that the polymer blend comprises a weight percentage of the composition having molecules with active hydrogen(s) in the range of 2-20, and preferably in the range 3-15 and most preferably in the range 5-10.

In order to obtain good mechanical properties, the substrate materials is preferably prepared and composed in such a way that it fulfills at least some of the following requirements, and preferably essentially all of them:

The material should have a hardness adequate for the intended use. For example for urinary catheter, the hardness Shore A should preferably be in the range 75-85, and most preferably within the range 78-82.

It is further preferred that the substrate has a melting temperature exceeding 90 deg. C., and preferably exceeding 110 deg. C., and most preferably exceeding 130 deg. C.

Possibility to be sterilized by known sterilization methods. In particular it is preferred that the substrate has a radiation resistance such that it can endure at least 50 kGy essentially without degradation, in order to enable radiation sterilization of the medical device.

The material should exhibit low resilience.

The material should have good kinking properties.

The composition should preferably be essentially free from chlorine or other halogens.

Preferably, the composition should essentially only comprise carbon, hydrogen, nitrogen and oxygen. These constituents should in combination exceed 90% in weight of the substrate material, and preferably exceed 95%. The amount of nitrogen is preferably less than 10%, and most preferably less than 5%.

The polymer should preferably be extrudable, or usable for molding, and in particular useable for injection molding.

The substrate material should preferably be biocompatible.

Good dimension stability. In particular, it is preferred that the longitudinal shrinkage of the catheters as a result of the coating process is less than 5%, and preferably less than 1%, of the original length.

DESCRIPTION OF PREFERRED COATING METHODS

Some preferred examples of methods for applying a hydrophilic surface coating to the substrate will now be discussed in greater detail. However, it is to be noted that the above-discussed substrate material can also be used for many other methods for obtaining a hydrophilic surface coating.

A preferred method for coating of the substrate will now be disclosed in more detail. The outer surface of the elongate shaft is preferably coated with a stable hydrophilic coating by applying sequentially to the surface of the substrate first a solution comprising between 0.05 to 40% (weight to volume) of an isocyanate compound and thereafter a solution containing between 0.5 and 50% (weight to volume) of polyvinylpyrrolidone and curing at an elevated temperature. The isocyanate solution may advantageously contain between 0.5 to 10% (weight to volume) of the isocyanate compound, and may preferably contain between 1 to 6% (weight to volume) of the isocyanate compound. Generally, the isocyanate solution only needs to be in contact with the surface briefly, for example 5 to 60 sec.

Application of the isocyanate solution to the substrate surface results in a coating having unreacted isocyanate groups being formed on the substrate surface. Application of the polyvinylpyrrolidone solution to the substrate surface then results in a hydrophilic polyvinylpyrrolidone-polyurea interpolymer coating being formed. Curing of this hydrophilic coating binds the isocyanate compounds together to form a stable non-reactive network that binds the hydrophilic polyvinylpyrrolidone. To advantage, curing takes place in the presence of a water-containing gas, for example ambient air, to enable the isocyanate groups to react with the water to yield an amine which rapidly reacts with other isocyanate groups to form a urea cross-link. Further, the method may comprise the steps of evaporating the solvent of the isocyanate solution prior to application of the polyvinylpyrrolidone solution and evaporating the solvent of the polyvinylpyrrolidone solution prior to curing of the hydrophilic coating. This may for example be done by air drying.

The isocyanate compound preferably comprises at least two unreacted isocyanate groups per molecule. The isocyanate may be selected from 2,4-toluene diisocyanate and 4,4'-diphenylmethane diisocyanate, or a pentamer of hexamethylene diisocyanate and toluene diisocyanate of cyanurate type, or trimerized hexamethylene diisocyanate biuret or mixtures thereof.

The solvent for the isocyanate compound is preferably one which does not react with isocyanate groups. A suitable solvent is methylene chloride but it is also possible to use ethyl acetate, acetone, chloroform, methyl ethyl ketone and ethylene dichloride, for example.

In order to shorten the necessary reaction times and curing times suitable catalysts for isocyanate curing may be added. These catalysts may be dissolved in either the isocyanate solution or the polyvinylpyrrolidone solution but are preferably dissolved in the latter. Different types of amines are especially useful, for example diamines, but also for example triethylenediamine. Preferably, an aliphatic amine is employed which is volatisable at the drying and curing temperatures used for the coating, and which furthermore is non-toxic. Examples of suitable amines are N,N' diethylethylendiamine, hexamethylendiamine, ethylendiarnine, paradiaminobenzene, 1,3-propandiol-para-aminobenzoic acid diester and diaminobicyclo-octane.

The polyvinylpyrrolidone preferably used has a mean molecular weight of between $10^4$ to $10^7$ with the most preferred mean molecular weight being about $10^5$. Polyvinylpyrrolidone having such a molecular weight is commercially available, for example under the trademark Kollidong (BASF). Examples of suitable solvents for polyvinylpyrrolidone that may be used are methylene chloride, ethyl acetate, acetone, chloroform, methyl ethyl ketone and ethylene dichloride. The proportion of polyvinylpyrrolidone in the solution is preferably between 0.5 to 10% (weight to volume) and most preferred between 2 to 8% (weight to volume). The polyvinylpyrrolidone in the solvent is applied by dipping, spraying or the like for a short period of time, e.g. during 5 to 50 sec.

Curing of the coating is preferably performed at a temperature of 50 to 130 deg. C., in for example an oven, for a duration of between 5 to 300 min.

In a preferred embodiment the hydrophilic coating contains an osmolality-increasing compound, for instance an inorganic salt selected from sodium and potassium chlorides, iodides, citrates and benzoates. The osmolality-increasing compound may be applied in the manner detailed in EP 0 217 771 by the same applicant.

EXPERIMENTS

In experimental tests, two different types of polyolefin-based substrates were used: Substrate A, being based on the commercially available polyolefin material Dryflex®, and Substrate B, being based on the commercially available polyolefin material Meliflex®. The substrate materials were made to fulfill the above-discussed mechanical requirements, such as having a hardness Shore A within the range 78-82.

For Substrate A, two different material compositions were used:

A first blend, Substrate A-0, consisting essentially only of polyolefin, and without polyamide or polyurethane, or the like.

A second blend, Substrate A-5/10, consisting of a blend of the material used in Substrate A-0 and polyurethane. The proportion of polyurethane in the polymer blend was in the range 5-10% (weight to volume).

For Substrate B, four different material compositions were used:

A first blend, Substrate B-0, consisting essentially only of polyolefin, and without polyamide or polyurethane, or the like.

A second blend, Substrate B-5, consisting of a blend of the material used in Substrate B-0 and polyamide. The proportion of polyamide in the polymer blend was about 5% (weight to volume).

A third blend, Substrate B-10, consisting of a blend of the material used in Substrate B-0 and polyamide. The proportion of polyamide in the polymer blend was about 10% (weight to volume).

A fourth blend, Substrate B-15, consisting of a-blend of the-material used in Substrate B-0 and polyamide. The proportion of polyamide in the polymer blend was about 15% (weight to volume).

The substrates were coated with a hydrophilic coating as discussed above. Consequently, the catheters are prepared by dipping PVC-catheters in a primer solution comprising a diisocyanate (named Desmodur IL.), which is dissolved in methylene chloride to a concentration of 2% (weight/volume), for 15 seconds. The catheters are thereafter dried at ambient temperature for 60 seconds, and are then dipped for 3 seconds in a solution containing 6% (weight/volume) of polyvinylpyrrolidone (PVP K90) dissolved in methylene chloride. The catheters are then allowed to flush off at 35 deg. C. for 30 minutes, and are then cured for 60 minutes at 80 deg. C., and are finally allowed to cool to room temperature and rinsed in water.

In a first line of experiments, the water retention of the catheters, differing only in the catheter substrate material being used, were tested for water retention in ambient air. To this end, the catheters were wetted during 30 sec., and the water content ($mg/cm^2$) in the hydrophilic coating was determined after 1 and 6 minutes, respectively. The water content was determined by weighing the catheters before wetting, to obtain a reference weight, and by measuring the catheters weights a certain time after wetting, and subtracting the reference weight from this subsequently measured weight. The obtained weight difference is a measure of the water content being held by the hydrophilic coating at the time of measurement.

Similar measurements were also made on catheters which were leached before the measurements. Consequently, these catheters were leached by placing the catheters in a water bath at 35 deg. C., during stirring of the water, for a duration of 30 min. After leaching, the catheters were dried for at least 24 h, and then used for subsequent testing. The leaching is a test on how strongly the hydrophilic surface coating adheres to the substrate. The result for a hydrophilic coating with a low adherence is that a large part of the coating is dissolved in the water (and only a minor part of the hydrophilic polymer remains as a coating on the substrate). A hydrophilic coating with a strong adherence will be much less affected by the leaching. For practical purposes, this is also important for the use situation. An adequate adherence, which in testing is only moderately affected by the leaching, will adhere better to the catheter surface when it is introduced into the urethra of a patient, thereby preserving the low-friction properties during the use and avoiding polymer residues in the urethra after use. Further, with such a catheter, the effect of exceeding the recommended wetting time is less severe and harmful, since this catheter will be less affected by-a prolonged wetting period.

The results of the water retention measurements are presented in Table 1 below.

TABLE 1

| | Water retention [$mg/cm^2$] at different times after wetting | | | |
|---|---|---|---|---|
| Catheter | Un-leached 1 min | Un-leached 6 min | Leached 1 min | Leached 6 min |
| A-0 | 4.7 | 1.5 | 1.5 | 0.3 |
| A-5/10 | 13.2 | 11.2 | 9.8 | 8.3 |
| B-0 | 4.5 | 1.7 | 1.3 | 0.4 |
| B-5 | 10.7 | 8.2 | 7.0 | 5.1 |
| B-10 | 11.4 | 9.4 | 7.1 | 5.2 |
| B-15 | 10.1 | 7.7 | 5.5 | 4.0 |

As is clearly evident from the measurements illustrated in table 1, the wetting fluid content in the catheters A-5/10, B-5, B-10 and B-15 are significantly higher than in the catheters A-0 and B-0. Thus, the water retention in the catheters having substrates including polyamide/polyurethane is apparently significantly improved over the water retention in the catheters having ordinary polyolefin-based substrates. Further, the measurements indicate that there is a significant improvement in water retention already at 5% polyamide/polyurethane in the substrate, whereas a further increase (compare B-5 to B-10) only lead to a moderate additional improvement, and at 15% starts to deteriorate slightly (see B-15). Further, it is notable that the water retention in the catheters A-5/10, B-5, B-10 and B-15 are only moderately lower for the leached catheters, whereas in the catheters A-0 and B-0 there is a dramatic deterioration in water retention after leaching.

For measuring friction and friction coefficient, the ASTM 1894-93 standard ("The Standard Test Method for Static and Kinetic Coefficient of Friction of Plastic Film and Sheeting") was used. In the measurement, the same types of catheters as in the experiment discussed in relation to table 1 were used, each 10 cm long, and placed 3 cm apart between two surfaces after having been wetted for 0.5 minute. The tubes or catheters, cut in lengths of 10 cm, were fixed on a stainless steel plate with two stainless steel rods as shown in ASTM D 1894-93. The rods had diameters comparable with the inner diameter of the tubes or catheters to keep their shape even when heavy sledges were placed upon them. The friction was measured immediately upon placement between the surfaces, and thereafter every second minute. The pulling force from the sledge was measured in Newtons. A mean friction value [N] is calculated over the distance, and a corresponding friction coefficient µ was calculated.

In Table 2, the results of measurements using different catheters for each reading are presented, and in Table 3 the corresponding friction coefficients are given.

TABLE 2

Friction force [N] at different times after wetting

| Catheter | A-0 | A-5/10 | B-0 | B-5 | B-10 | B-15 |
|---|---|---|---|---|---|---|
| Initially | 0.523 | 0.077 | 0.914 | 0.072 | 0.101 | 0.157 |
| 2 min | 0.613 | 0.074 | 1.174 | 0.088 | 0.086 | 0.195 |
| 4 min | 0.588 | 0.075 | 0.841 | 0.088 | 0.109 | 0.161 |
| 6 min | 0.516 | 0.073 | 1.283 | 0.150 | 0.159 | 0.109 |
| 8 min | 0.697 | 0.087 | 1.487 | 0.110 | 0.159 | 0.133 |
| 10 min | 1.023 | 0.088 | 1.731 | 0.104 | 0.216 | 0.192 |
| 20 min | Dry | 0.156 | Dry | 0.269 | 0.297 | 0.474 |

TABLE 3

Friction coefficient, µ, at different times after wetting

| Catheter | A-0 | A-5/10 | B-0 | B-5 | B-10 | B-15 |
|---|---|---|---|---|---|---|
| Initially | 0.266 | 0.039 | 0.466 | 0.037 | 0.051 | 0.080 |
| 2 min | 0.313 | 0.038 | 0.599 | 0.045 | 0.044 | 0.099 |
| 4 min | 0.300 | 0.038 | 0.429 | 0.045 | 0.056 | 0.082 |
| 6 min | 0.263 | 0.037 | 0.654 | 0.076 | 0.081 | 0.056 |
| 8 min | 0.355 | 0.045 | 0.758 | 0.056 | 0.055 | 0.068 |
| 10 min | 0.521 | 0.045 | 0.882 | 0.053 | 0.110 | 0.054 |
| 20 min | Dry | 0.080 | Dry | 0.137 | 0.151 | 0.242 |

As is clearly evident from the measurements illustrated in tables 2 and 3, the friction force and friction coefficient in the catheters A-5/10, B-5, B1-10 and B1-15 are significantly improved compared to the catheters A-0 and B-0. Thus, the catheters having substrates including polyamide/polyurethane are apparently significantly improved in respect of initial low-friction properties of the catheter when wetted, and in maintaining this low-friction state for an extended period of time. Further, the measurements indicate that these significant improvements appear already at 5% polyamide/polyurethane in the substrate, whereas a further increase (compare B-5 to B-10) lead to no significant effect in terms of friction, and at 15% the friction values start to deteriorate slightly (see B-15).

Usability, comfort, manageability, etc. are naturally relatively subjective properties of the catheters, and are consequently difficult to evaluate objectively. However, attempts have been made to make at least some experimental evaluations regarding these properties.

In these experiments, 21 experienced users of intermittent catheters with different degree of dexterity were provided with catheters of five different types, each catheter type having different substrate materials. Apart from the substrate materials, the catheters were prepared in the same way, corresponding to the method discussed above, and were thus, apart from the specific substrate materials, essentially identical. In each of the different catheters, one of the following substrate materials was used: PVC (poly vinyl chloride), TPU (thermoplastic polyurethane), PEBA (polyether-block-polyamide), and the previously discussed A-5/10 and B-10.

In a first usability test, the users were individually to rank the five catheter types, from 1 to 5, on the basis of which catheter they would rather use. For this ranking, "1" was afforded to the catheter that the user would prefer to use, and "5" to the catheter that was least preferred. Average values of all the rankings from the testers were calculated, and the result is presented in the table 4 below.

TABLE 4

Subjective ranking of usability by experienced users

| Catheter | Average ranking value |
|---|---|
| PVC | 2.6 |
| TPU | 2.9 |
| PEBA | 3.9 |
| A-5/10 | 3.1 |
| B-10 | 2.4 |

Interesting observations that can be made from this experiment is that the users actually, as an average, prefer the B-10 catheter over all the other catheters. Further, from a usability point of view, the PVC and B-10 catheters are significantly more preferred than the rest of the catheters. Further, it is noted that ranking values for the A-5/10 and TPU catheters are essentially equal, and both are significantly more preferred than the PEBA catheter.

In another line of experiments, the same 21 experienced users were given the assignment of trying to introduce catheters into an artificial urethra in an ordinary way, and as fast as possible. Three catheters of each type were used, and the time it took for the users to maneuver the catheter into an inserted position was measured. Thus, 63 measurements were made for each catheter type, and the average insertion time for each catheter type is presented in the table 5 below.

TABLE 5

Insertion time into artificial urethra

| Catheter | Average insertion time (s) |
|---|---|
| PVC | 4.8 |
| TPU | 5.3 |
| PEBA | 6.4 |
| A-5/10 | 5.5 |
| B-10 | 5.0 |

Interesting observations that can be made from this experiment is that the average insertion time was lowest for the PVC catheter, and, thus, that the PVC catheter was best in this respect. However, it is also seen that the B-10 catheter is nearly as good, having an average insertion time that is only 4% higher. Further, the average insertion times for the TPU and A-5/1 0 catheters are comparable to each other, and slightly larger than for the PVC and B-10 catheters (the average insertion times being 11% and 16% longer, respectively, than for PVC). As before, the PEBA catheters were significantly poorer, having an average insertion time-which is about 34% higher than for a PVC catheter.

Thus, it may be generally concluded that the usability and maneuver properties of the new catheter substrates are as good, or even better, than previously used catheter substrates, such as are presently used in commercially available urinary catheters for intermittent use.

CONCLUSION AND SUMMARY

The invention has now been discussed in relation to different embodiments. However, it should be appreciated by those versed in the art that several further alternatives are possible. For example, the features of the different embodiments discussed above may naturally be combined in many other ways.

It is further possible to use the invention for other types of catheters than urinary catheters, such as vascular catheters or the like.

Many different materials could also be used for the different parts of the catheter assembly. Specifically, different blends of polyolefin and other constituents may be used, and many different compositions having molecules with active hydrogen(s) are feasible. Further, many different types of hydrophilic coatings may be used for coating the substrate.

It will be appreciated by those versed in the art that several such alternatives similar to those described above could be used without departing from the spirit of the invention, and all such modifications should be regarded as a part of the present invention, as defined in the appended claims.

The invention claimed is:

1. A urinary catheter comprising:
   an elongate tubular shaft made of a substrate, having on its surface, on at least a part thereof, a hydrophilic surface layer providing low-friction surface character of the urinary catheter when wetted by a wetting fluid,
   wherein the whole substrate is made of a polymer blend comprising a polyolefin and a composition having molecules with active hydrogen(s), the composition having molecules with active hydrogen(s) being at least one of amines and urethanes, and
   wherein the polymer blend comprises at least 80 weight percent polyolefin or polyolefin intermixed with medical oil and/or paraffin.

2. The urinary catheter of claim 1, wherein the composition having molecules with active hydrogen(s) is a polymer having active hydrogen(s).

3. The urinary catheter of claim 1, wherein the composition having molecules with active hydrogen(s) is polyurethane.

4. The urinary catheter of claim 1, wherein the substrate has a hardness Shore A in the range 75-85.

5. The urinary catheter of claim 4, wherein the substrate has a hardness Shore A in the range 78-82.

6. The urinary catheter of claim 1, wherein the substrate has a melting temperature exceeding 90 deg. C.

7. The urinary catheter of claim 6, wherein the substrate has a melting temperature exceeding 110 deg. C.

8. The urinary catheter of claim 6, wherein the substrate has a melting temperature exceeding 130 deg. C.

9. The urinary catheter of claim 1, wherein the polymer blend of the substrate is essentially free from chlorine or other halogens.

10. The urinary catheter of claim 1, wherein the substrate has a radiation resistance such that it can endure at least 50 kGy essentially without degradation.

11. The urinary catheter of claim 1, wherein the polyolefin comprises at least one polymer selected from the group: polyethylene, polypropylene, and styrene block copolymer (SEBS).

12. The urinary catheter of claim 1, wherein the hydrophilic surface layer is adhered to the substrate by a polyurea network,
   whereby said polyurea network forms a covalent bond to said active hydrogen(s) in the substrate.

13. The urinary catheter of claim 1, wherein the hydrophilic surface layer is adhered to the substrate by a polyester or epoxy network, whereby said network forms a covalent bond to said active hydrogen(s) in the substrate.

14. The urinary catheter of claim 1, wherein the substrate consists of a polymer blend of polyolefin and a composition having molecules with active hydrogen(s).

15. The urinary catheter of claim 1, wherein the polymer blend comprises a weight percentage of the composition having molecules with active hydrogen(s) in the range of 2-20.

16. The urinary catheter of claim 15, wherein the polymer blend comprises a weight percentage of the composition having molecules with active hydrogen(s) in the range 3-15.

17. The urinary catheter of claim 15, wherein the polymer blend comprises a weight percentage of the composition having molecules with active hydrogen(s) in the range 5-10.

18. The urinary catheter of claim 1, wherein the polyolefin comprises at least one polymer selected from the group: polypropylene and styrene block copolymer (SEBS).

19. The urinary catheter of claim 2, wherein the polyolefin comprises at least one polymer selected from the group: polypropylene and styrene block copolymer (SEBS).

20. The urinary catheter of claim 1, wherein the material of the substrate comprises at least 90% in weight of carbon, hydrogen, nitrogen and oxygen, and less than 10% of nitrogen.

21. The urinary catheter of claim 1, wherein the material of the substrate comprises at least 95% in weight of carbon, hydrogen, nitrogen and oxygen, and less than 5% of nitrogen.

* * * * *